US006355859B1

(12) United States Patent
Bosworth et al.

(10) Patent No.: US 6,355,859 B1
(45) Date of Patent: Mar. 12, 2002

(54) **INTERACTIONS BETWEEN GENOTYPE AND DIET IN SWINE THAT PREVENT *E. COLI* ASSOCIATED INTESTINAL DISEASE**

(75) Inventors: Brad Bosworth, Cambride (GB); Julia Ridpath, Gilbert, IA (US); Barry Wiseman, Belle Mead, NJ (US)

(73) Assignees: Biotechnology Research and Development Corporation, Peoria, IL (US); The United States of America as represented by the Department of Agriculture, Washington, DC (US)

( * ) Notice: Subject to any disclaimer, the term of this patent is extended or adjusted under 35 U.S.C. 154(b) by 0 days.

(21) Appl. No.: 09/151,592

(22) Filed: Sep. 18, 1998

Related U.S. Application Data
(60) Provisional application No. 60/047,181, filed on May 27, 1997, now abandoned.

(51) Int. Cl.[7] ...................... A01K 67/00; A01K 67/033; C07H 21/02; C07H 21/04; A61K 49/00
(52) U.S. Cl. .................. 800/8; 536/23.1; 536/23.5; 424/9.1
(58) Field of Search .............. 800/8; 536/23.1, 536/23.5; 424/9.1; 426/635

(56) References Cited

U.S. PATENT DOCUMENTS

| | | | |
|---|---|---|---|
| 5,358,649 A | 10/1994 | MacLennan et al. ............ | 435/6 |
| 5,431,928 A | * 7/1995 | Saito et al. ..................... | 426/2 |
| 5,552,144 A | 9/1996 | Samuel et al. ............ | 424/236.1 |
| 5,575,999 A | * 11/1996 | Yoder ........................ | 424/94.6 |
| 5,814,333 A | * 9/1998 | Onishi et al. ............... | 424/442 |

FOREIGN PATENT DOCUMENTS

| | | | |
|---|---|---|---|
| WO | WO 86/04604 | 8/1986 | |
| WO | WO 94/13811 | 6/1994 | |
| WO | WO 94 21142 A | 9/1994 | |
| WO | WO 96/28967 | 9/1996 | |
| WO | WO 98/53101 | * 5/1998 | ............ C12Q/1/68 |
| WO | WO 99 07236 A | 2/1999 | |

OTHER PUBLICATIONS

Nollet, H. et al. (1999) "Protection of just weaned pigs against infection with f18+ *Escherichia coli* by non–immune plasma powder," *Veterinary Microbiology* 65: 37–45.

Van Heugten, E. et al. (1994) "The effect of dietary protein on performance and immune response in weanling pigs subjected to an inflammatory challenge," *Journal of Animal Science* 72: 2661–2669.

Vogeli et al. (1997) "Ein molekular test fur den nachweis des *E. coli* F18 rezeptors: ein durchbruch im kamf gegen oedemkrakheit und absetzdurchfall beim schwein," *Schweizer Archiv fur Tierheilkunde* 139: 479–484.

De Rodas, B. Z. et al. (1995) "Plasma protein for pigs weaned at 19 to 24 days of age: effect on performance and plasma insulin–like growth factor I, growth hormone, insulin, and glucose concentrations," *Journal of Animal Science* 73: 3657–3665.

Li D.F. et al. (1991) et al. "Measuring suitability of soybean products for early–weaned pigs with immunological criteria," *Journal of Animal Science* 69: 3299–3307.

Bosworth BT, et al. Vaccination with Genetically Modified Shiga–Like Toxin Iie Prevents Edema Disease in Swine. Infection and Immunity. 1996. 64 (1): 55–60.

Cohney S, et al. Molecular Cloning of the Gene Coding for Pig $\alpha 1 \rightarrow 2$fucosyltransferase. Immunogenetics. 1996. 44: 76–79.

Devereux J, et al. A Comprehensive Set of Sequence Analysis Programs for the VAX. Nucleic Acids Research. 1984. 12 (1): 387–395.

Fujii J. et al. Identification of a Mutation in Porcine Ryanodine Receptor Associated with Malignant Hyperthemia. Science. 1991. 253: 448–451.

Kelly RJ, et al. Molecular Basis for Hblood Group Deficiency in Bombay $(O_h)$ and Para–Bombay Individuals. Proc Natl Acad Sci. 1994. 91: 5843–5847.

Nagy B, et al. Susceptibility of Porcine Intestine to Pilus–Mediated Adhesion by Some Isolates of Piliated Enterotoxigenic *Escherichia coli* Increases with Age. Infection and Immunity. 1992. 60(4): 1285–1294.

Vögeli P, et al. Genes Specifying Receptors for F18 Fimbriated *Escherichia coli*, Causing Odema Disease and Postweaning Diarrhoea in Pigs, Map to Chromosome 6. Animal Genetics. 1996. 27: 321–328.

Kats et al. The effects of spray–dried blood meal on growth performance of the early–weaned pig. J. Anim Sci, vol. 72, pp. 2860–2869, Nov. 1994.*

(List continued on next page.)

*Primary Examiner*—Deborah J. R. Clark
*Assistant Examiner*—Peter Paras, Jr.
(74) *Attorney, Agent, or Firm*—Barnes & Thornburg; Alice O. Martin

(57) ABSTRACT

The present invention relates interactions between genotype and diet that are useful in the dietary control of intestinal disease. Compositions are related that are useful to differentiate, with a high level of sensitivity and specificity, swine that are genetically resistant to a reduced rate of weight gain when fed diets containing high levels of SBM. The reduced rate of gain can be prevented by reducing the levels of SBM in nursery diets and replacing a majority of the soy bean meal with animal-based protein sources, fish meal, plasma or milk. Genetically resistant swine fed either the diet low in SBM, or a diet high in SBM, and susceptible swine fed a diet low in SBM, were not colonized by F18+*E. coli* and gained weight at an acceptable rate.

5 Claims, 6 Drawing Sheets

OTHER PUBLICATIONS

Li, D.F., et al. Measuring Suitability of Soybean Products for Early–Weaned Pigs with Immunological Criteria, Journal of Animal Science 69:3299–3307, 1991.*

Sarmiento, J.I., et al. Postweaning diarrhea in swine: Effects of oxytetracycline on enterotoxigenic *Escherichia coli* infection. American Journal of Veterinary Research 49(7):1160–1163, Jul. 1988.*

Naylor, J.M., et al. Large Animal Clinical Nutrition. Mosby Yearbook, St. Louis, 1991.*

Radostits, O.M., et al. Herd Health: Food Animal Production Medicine, 2nd Edition. W.B. Saunders Company, Philadelphia, 1994.*

* cited by examiner

FIG.1

```
                        M   W   V   P   S   R   R   H   L   C   L   T   F   L   L   V   C     17
CT  CGA GCC ATG TGG GTC CCC AGC CGC CGC CAC CTC TGT CTG ACC TTC CTG CTA GTC TGT                 59

V   L   A   A   I   F   F   L   N   V   Y   Q   D   L   F   Y   S   G   L   D                 37
GTT TTA GCA GCA ATT TTC TTC CTG AAC GTC TAT CAA GAC CTC TTT TAC AGT GGC TTA GAC                119

L   L   A   L   C   P   D   H   N   V   V   S   S   P   V   A   I   F   C   L                 57
CTG CTG GCC CTG TGT CCA GAC CAT AAC GTG GTA TCA TCT CCC GTG GCC ATA TTC TGC CTG                179

A   G   T   P   V   H   P   N   A   S   D   S   C   P   K   H   P   A   S   F                 77
GCG GGC ACG CCG GTA CAC CCC AAC GCC TCC GAT TCC TGT CCC AAG CAT CCT GCC TCC TTT                239

S   G   T   W   T   I   Y   P   D   G   R   F   G   N   Q   M   G   Q   Y   A                 97
TCC GGG ACC TGG ACT ATT TAC CCG GAT GGC CGG TTT GGG AAC CAG ATG GGA CAG TAT GCC                299

T   L   L   A   L   A   Q   L   N   G   R   Q   A   F   I   Q   P   A   M   H                117
ACG CTG CTG GCC CTG GCG CAG CTC AAC GGC CGC CAG GCC TTC ATC CAG CCT GCC ATG CAC                359

A   V   L   A   P   V   F   R   I   T   L   P   V   L   A   P   E   V   D   R                137
GCC GTC CTG GCC CCC GTG TTC CGC ATC ACG CTG CCT GTC CTG GCG CCC GAG GTA GAC AGG                419

H   A   P   W   R   E   L   E   L   H   D   W   M   S   E   D   Y   A   H   L                157
CAC GCT CCT TGG CGG GAG CTG GAG CTT CAC GAC TGG ATG TCC GAG GAT TAT GCC CAC TTA                479

K   E   P   W   L   K   L   T   G   F   P   C   S   W   T   F   F   H   H   L                177
AAG GAG CCC TGG CTG AAG CTC ACC GGC TTC CCC TGC TCC TGG ACC TTC TTC CAC CAC CTC                539

R   E   Q   I   R   S   E   F   T   L   H   D   H   L   R   Q   E   A   Q   G                197
CGG GAG CAG ATC CGC AGC GAG TTC ACC CTG CAC GAC CAC CTT CGG CAA GAG GCC CAG GGG                599

V   L   S   Q   F   R   L   P   R   T   G   D   R   P   S   T   F   V   G   V                217
GTA CTG AGT CAG TTC CGT CTA CCC CGC ACA GGG GAC CGC CCC AGC ACC TTC GTG GGG GTC                659

H   V   R   R   G   D   Y   L   R   V   M   P   K   R   W   K   G   V   V   G                237
CAC GTG CGC CGC GGG GAC TAT CTG CGT GTG ATG CCC AAG CGC TGG AAG GGG GTG GTG GGT                719

D   G   A   Y   L   Q   Q   A   M   D   W   F   R   A   R   Y   E   A   P   V                257
GAC GGC CGT TAC CTC CAG CAG GCT ATG GAC TGG TTC CGG GCC CGA TAC GAA GCC CCC GTC                779

F   V   V   T   S   N   G   M   E   W   C   R   K   N   I   D   T   S   R   G                277
TTT GTG GTC ACC AGC AAC GGC ATG GAG TGG TGC CGG AAG AAC ATC GAC ACC TCC CGG GGG                839

D   V   I   F   A   G   D   G   R   E   A   A   P   A   R   D   F   A   L   L                297
GAC GTG ATC TTT GCT GGC GAT GGG CGG GAG GCC GCG CCC GCC AGG GAC TTT GCG CTG CTG                899

V   Q   C   N   H   T   I   M   T   I   G   T   F   G   F   W   A   A   Y   L                317
GTG CAG TGC AAC CAC ACC ATC ATG ACC ATT GGC ACC TTC GGC TTC TGG GCC GCC TAC CTG                959

A   G   G   D   T   I   Y   L   A   N   F   T   L   P   T   S   S   F   L   K                337
GCT GGT GGA GAT ACC ATC TAC TTG GCT AAC TTC ACC CTG CCC ACT TCC AGC TTC CTG AAG               1019

I   F   K   P   E   A   A   F   L   P   E   W   V   G   I   N   A   D   L   S                357
ATC TTT AAA CCC GAG GCT GCC TTC CTG CCC GAG TGG GTG GGC ATT AAT GCA GAC TTG TCT               1079

P   L   Q   M   L   A   G   P   *   (SEQ ID NO:13)                                            365
CCA CTC CAG ATG TTG GCT GGG CCT TGA ACC AGC CAG GAG CCT TTC TGG AAT AGC CTC GGT               1139

CAA CCC AGG GCC AGC GTT ATG GGT CTC CGG AAG CCC GAG TAA CTT CCG GAG ATG CTG GTG               1199

GTC CTG TAG CAG GCT GGA CAC TTA TTT CAA GAG TGA TTC TAA TTG GCT GGA CTC AGA GGA               1259

AAC CCT GCA G  (SEQ ID NO:12)                                                                 1269
```

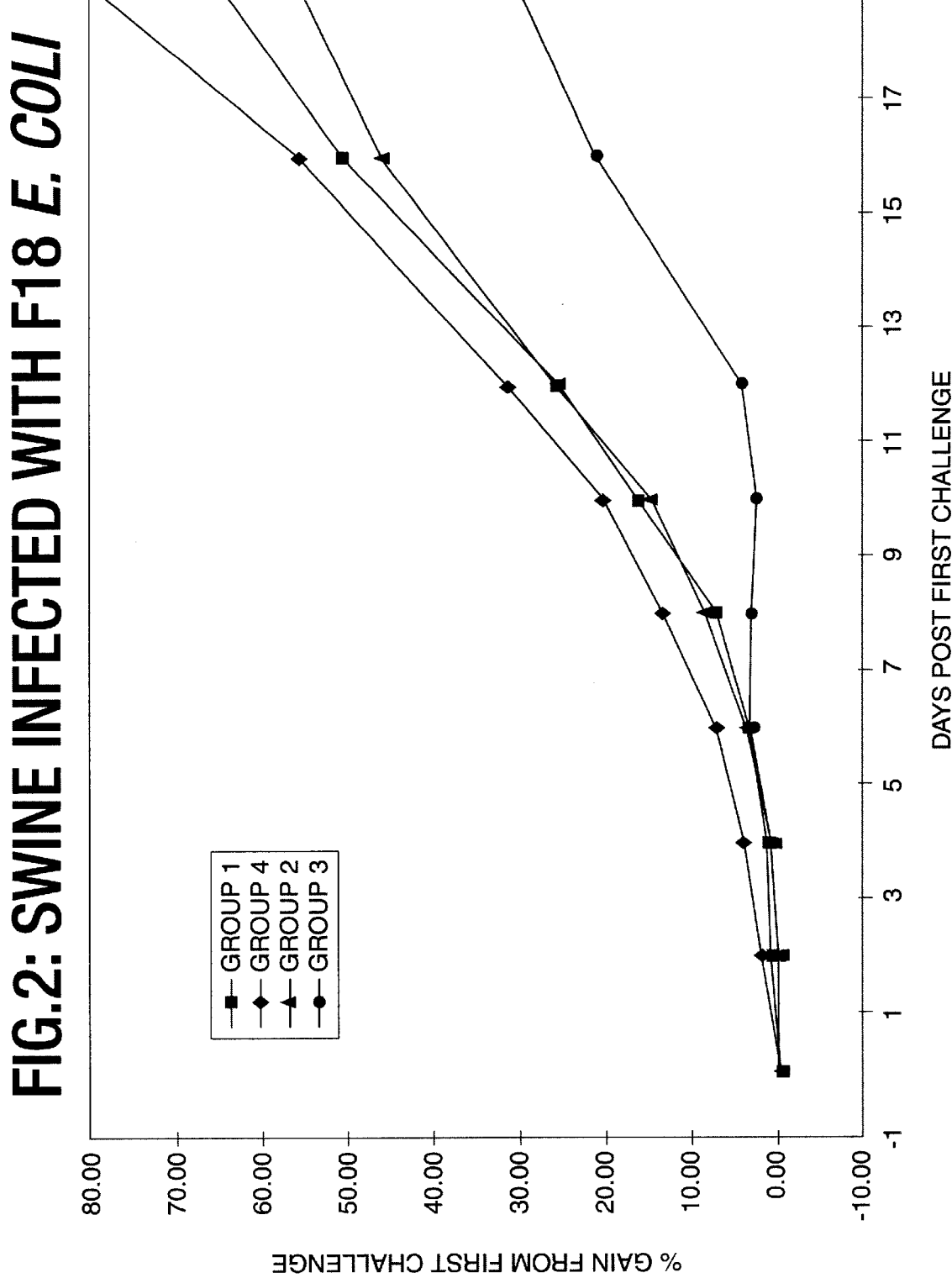

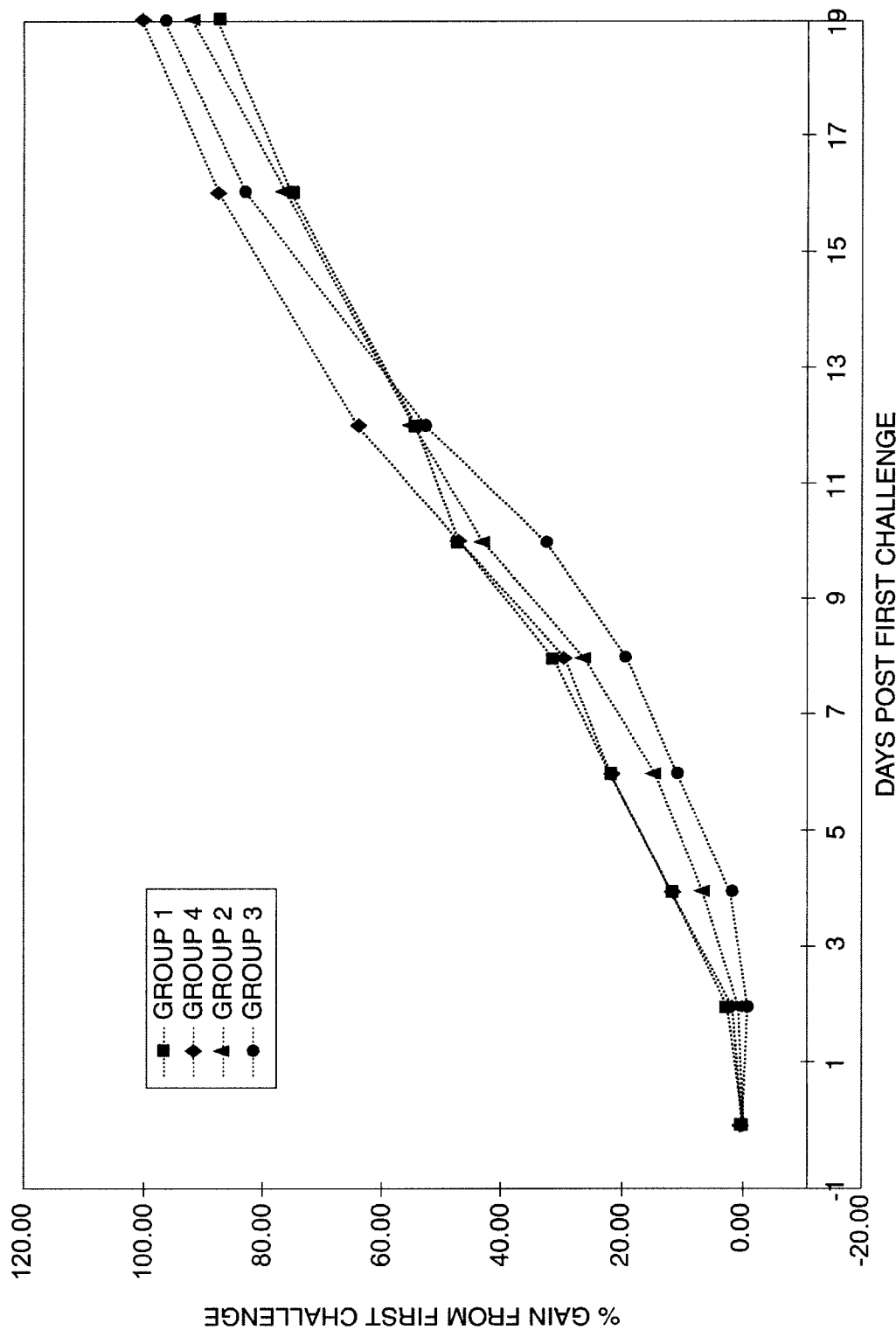
FIG.3: SWINE NOT INFECTED WITH F18 E. COLI

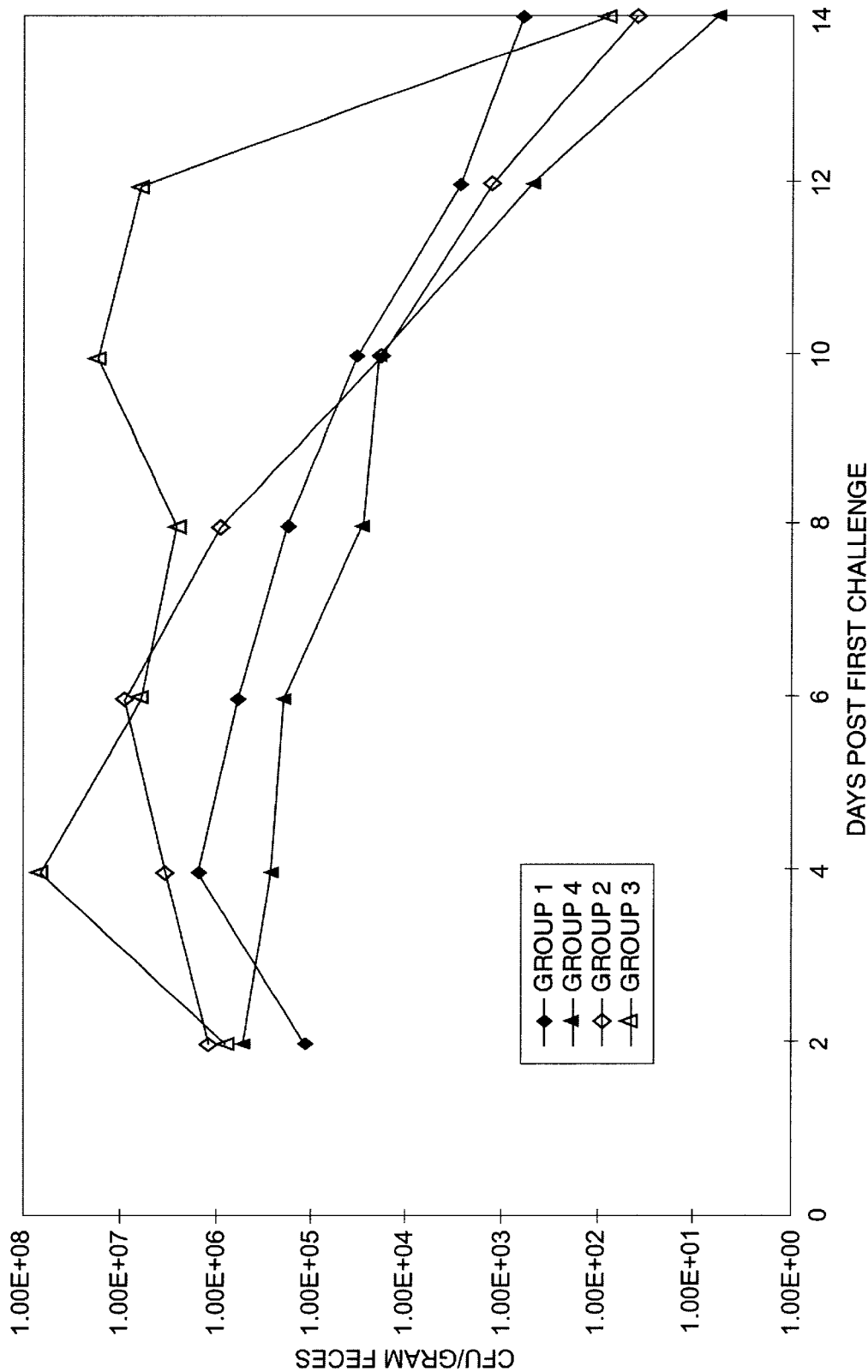

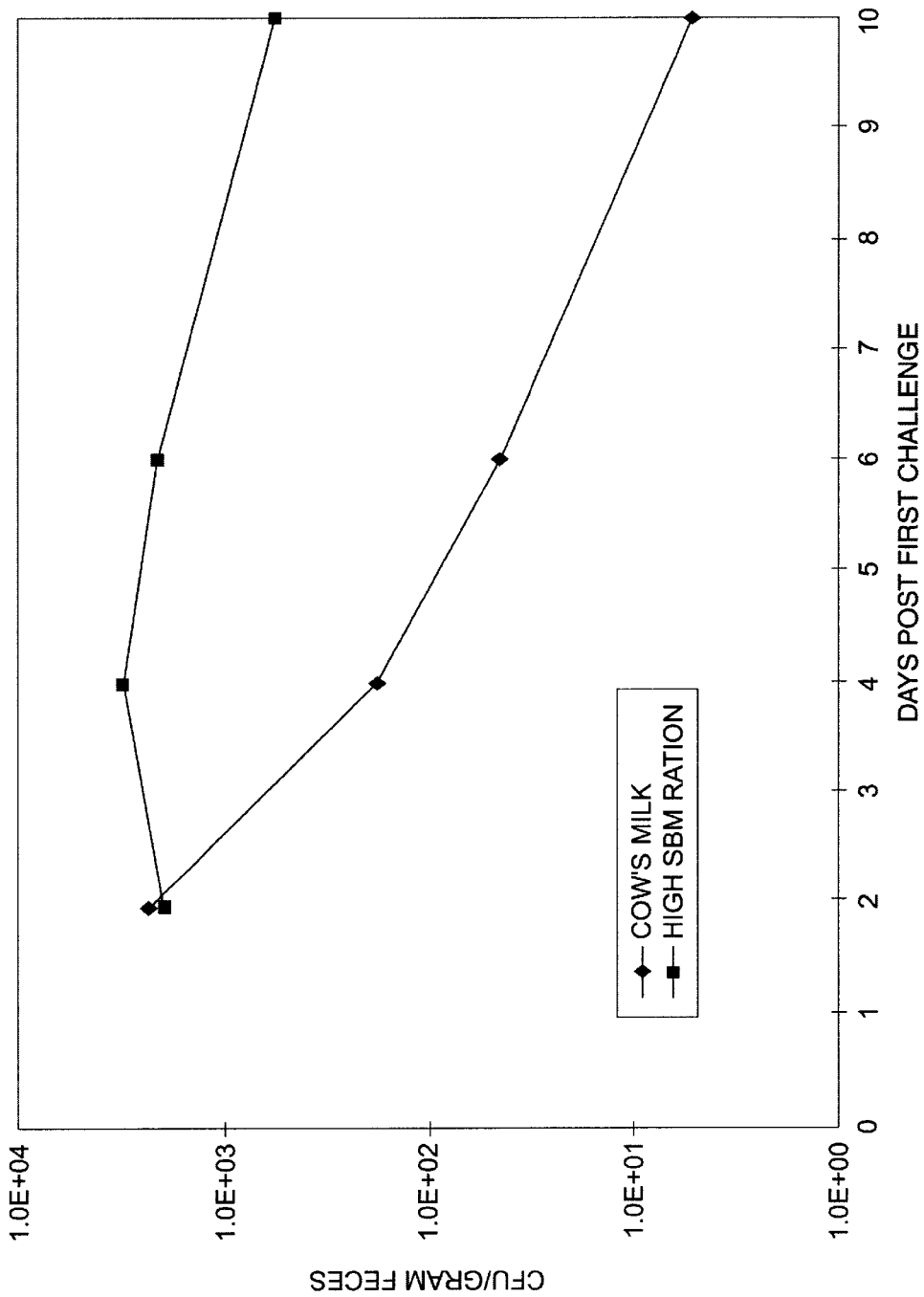
FIG. 5: SHEDDING OF F18 E. COLI IN INFECTED SWINE

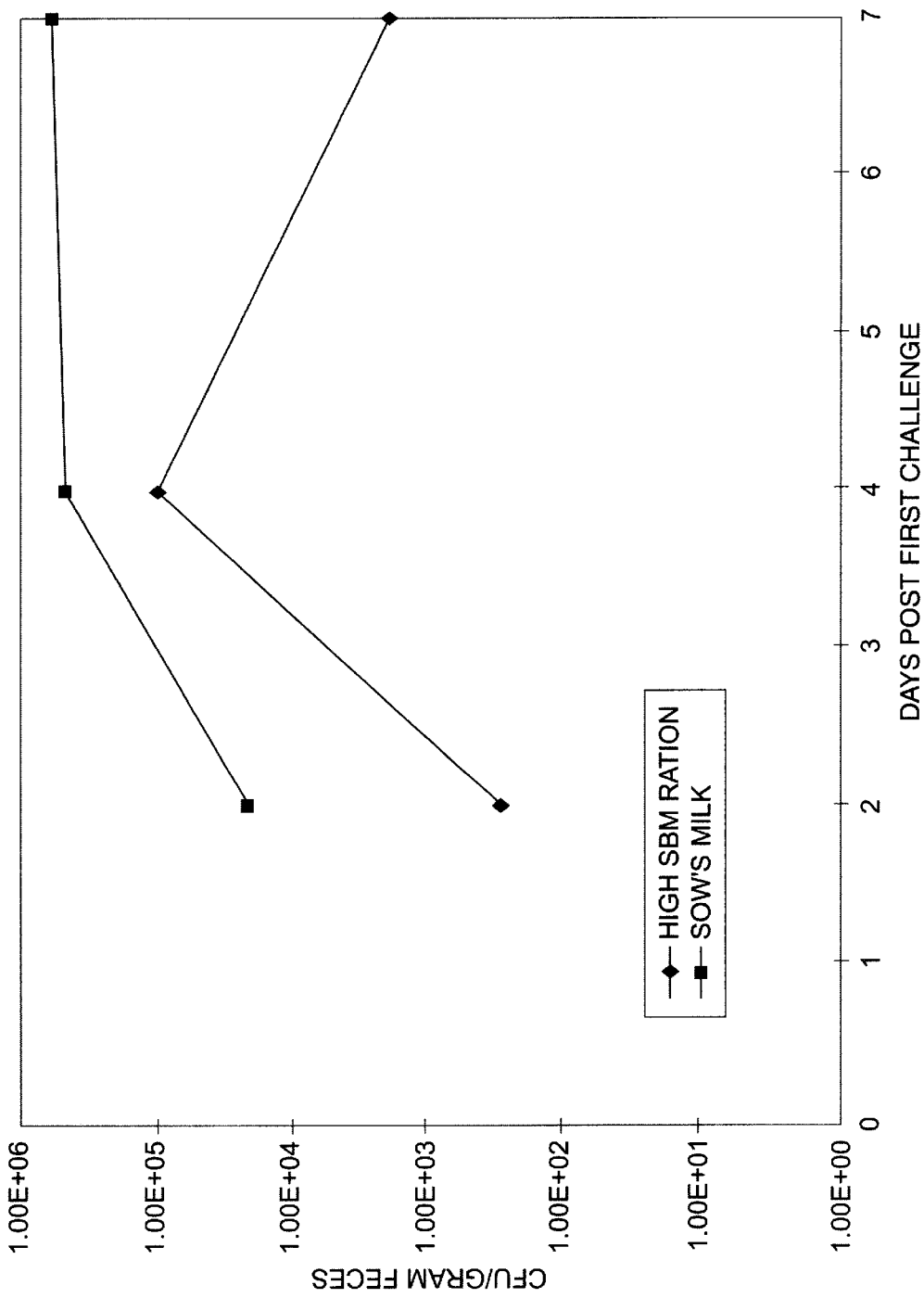

INTERACTIONS BETWEEN GENOTYPE AND DIET IN SWINE THAT PREVENT *E. COLI* ASSOCIATED INTESTINAL DISEASE

This application claims priority from copending PCT US 98/10318 and US 98/10259, filed May 20, 1998, which claim priority from U.S. Ser. No. 60/047,181 filed May 27, 1997, now abandoned.

BACKGROUND OF THE INVENTION

This invention relates interactions between genotype and diet in swine that prevent *E. coli* associated intestinal disease. Methods and compositions are provided for identifying swine which are genetically able to utilize low cost feed stuffs and feed compositions to prevent intestinal disorders after weaning.

Disease caused by F18+*E. coli* can be prevented by reducing the amount of soy bean meal (SBM) and total protein in the diet; however, this decrease in the total protein content of the pig's diet results in decreased quality e.g. weight (Bosworth et al., 1996; Bertschinger et al., 1979). Therefore, this treatment for F18+*E. coli* is not economical. Diets that prevent disease due to F18+*E. coli* but still contain high enough protein levels to allow swine to gain weight rapidly after weaning would be desirable.

Reduction of costs in swine production is a goal of breeders. Two of the most significant costs associated with swine production relate to food and disease, especially in the postweaning period. Intestinal diseases reduce weight gain, hence decrease the value of the swine. Treatment costs also occur. Swine weaned early require a high amount of protein in their diet in order to gain weight adequately, and the source of the protein is a major food diet cost. Plant-based sources high in protein content, typically soy bean meal (SBM), are common ingredients in most swine diets and are cheaper than animal-based sources, such as fish meal and blood meal. However, swine fed diets with high levels of SBM frequently have a reduced rate of weight gain relative to swine fed nursery diets postweaning in which a portion of the SBM is replaced with animal byproducts, such as whey and plasma (Li et al., 1991). The mechanisms responsible for this reduced rate of gain in recently weaned swine are not defined, but it could be that SBM acts as a food allergen in recently weaned swine who have just been removed from a diet high in animal protein (i.e., sows' milk).

A major problem in breeding swine is to keep them disease-free. Intestinal disorders postweaning are a particular problem. Intestinal disease is manifest in swine infected with F18 *E. coli* who may get either diarrhea and/or edema disease after weaning. Newborn swine are resistant to disease due to F18 *E. coli* because they do not express intestinal receptors for this *E. coli* and thus, the *E. coli* is unable to adhere to and grow (colonize) the intestine of newborn swine (Nagy et al, 1992). F18 *E. coli* can also cause a mild subclinical disease, which results in a decreased rate of gain after weaning, but may cause no other detectable clinical signs (Bosworth et al., 1996). Swine suffering from subclinical disease also have very mild vascular damage in the brain and intestines, problems only detectable by thorough histologic examination performed by an experienced investigator.

A limited number of serotypes of toxigenic *Escherichia* (*E.*) *coli* strains are the causative agents of oedema disease and postweaning diarrhea in swine which induce serious economic losses, especially among piglets aged 4 to 12 weeks, in swine breeding farms all over the world. The typical clinical symptoms of oedema disease are neurological signs such as ataxia, convulsions and/or diarrhea. At post mortem examination, oedema is typically present at characteristic sites such as eyelids and forehead, stomach wall and mesocolon. The diseases are caused by Shiga-like toxin-II variant and enterotoxins LT, STa, STb respectively, produced by *E. coli* that colonize the surface of the small intestine without effecting major morphological changes of the enterocytes (cells in the intestine). Types of bacterial *E. coli* strains, such as F4, F18 and K88 are major lethal villains in this regard. "Oedema disease of swine is an enterotoxaemia characterized by generalized vascular damage. The latter is caused by a toxin, Shiga-like toxin II variant, produced by certain strains of *E. coli*" (Bertschinger et al., 1993). The *E. coli* are distinguished by their pili types, a group of adhesive fimbriae that are related are designated e.g., K88 or F18 (Vögeli et al., 1996).

Not all swine succumb to *E. coli* infections. Colonization depends on adherence of the bacteria to the enterocytes which is mediated by the bacterial fimbriae designated e.g., K88 or F18. Susceptibility to adhesion, i.e. expression of receptors in swine for binding the fimbriae, has been shown to be genetically controlled by the host and is inherited as a dominant trait with, in the case of F18, B being the susceptibility allele and b the resistance allele. (Vögeli et al., 1996; Meijerink et al., 1996). The genetic locus for this *E. coli* F18-receptor (ECF18R) has been mapped to porcine chromosome 6 (SSC6), based on its close genetic linkage to the S locus and other loci of the halothane (HAL) linkage group on chromosome 6. The receptor for K88 *E. coli* is on chromosome 13.

The mechanism for resistance appears to be that intestinal borders in resistant animals are not colonized by *E. coli*, i.e., the bacteria do not adhere to intestinal walls of resistant swine. Glycoprotein receptors in the brush border membrane of the intestine were shown to be responsible for the differences between adhesive and non-adhesive phenotypes related to some *E. coli*, therefore, the genotype of the host swine determines resistance. The fimbriated bacteria also have been studied. (WO 9413811)

Current methods of identifying swine that are resistant to F18 *E. coli* associated diseases are either to 1) collect intestinal samples from swine at slaughter and perform the microscopic adhesion test, (see Example 2 herein) 2) challenge the animals with virulent *E. coli* ("colonization test"), or 3) perform blood typing of the A-O(S) blood group system. The first two methods are not practical for identifying resistant animals for use as breeding stock. Although the blood typing method does identify resistant animals, the test is unable to determine whether susceptible animals are homozygous or heterozygous for susceptibility. At least two alleles (condition of a gene) at the receptor locus control either susceptibility (dominant) or resistance (recessive). Knowledge of the genotype of animals with regard to these alleles is essential to develop a successful breeding program. The purpose of the breeding program is to produce swine that are resistant to F18 *E. coli* associated diseases that decimate stock post-weaning.

In one publication the authors stated, in reference to oedema disease in swine, that "Searches are underway for appropriate genetic markers . . . " (Bertschinger et al., 1993, page 87) and, citing Walters and Sellwood, 1982:

Breeding resistant swine is an attractive method for prevention of diseases for which an effective prophylaxis is not available. The feasibility of this approach will depend on the prevalence of the gene(s) encoding resistance in the pig population, improved methods for the detection of resistant swine, and absence of negative genetic traits co-selected with this resistance.

A genetic "marker" locus is a coding or non-coding locus that is close to a genetic locus of interest, but is not necessarily the locus itself. Detectable phenotypes include restriction length fragment polymorphisms, colorimetric or enzymatic reactions, and antibiotic resistance. The S locus controls expression of the A and O blood group antigens. Swine homozygous recessive at the S locus do not express either A or O blood group antigens. A similar condition exists in humans and is due to mutations in the alpha (1,2) fucosyltransferase gene which encodes the human blood group H (Kelly et al., 1994; see also WO 9628967). The porcine alpha (1,2) fucosyltransferase gene of swine has recently been sequenced (Cohney et al., 1996). This gene is very likely the gene present at the S locus in swine.

The blood group H and Se loci have been mapped genetically and physically to human chromosome 19q13.3. This region is evolutionarily conserved, containing genes homologous to the HAL linkage group of genes in swine. The blood group H encoding gene is the so called FUT1 whereas the Se gene is equivalent to the FUT2 gene. FUT1 determines H antigen expression in the erythroid cell lineage, whereas FUT2 regulates expression of the H antigen in the secretory epithelia and saliva. Conservation of the FUT1 gene has been shown in lower mammals such as rat and rabbit, and mRNA expression has been shown in rabbit brain tissue and rat colon. In all these species two types of alpha (1,2) fucosyltransferase genes have been reported which are structurally very similar to the human FUT1 and FUT2 genes, but in particular the FUT1 homologous genes show a species specific expression pattern. In humans the FUT1 gene is responsible for synthesis of H antigens in the precursors of erythrocytes. However, in swine erythrocytes passively adsorb H-like antigens from the serum, as is the case for the human Lewis antigens. In swine all H-like antigens are related to exocrine secretory tissues, and expression of the FUT2 (Secretor) gene is seen in secretory tissue of other animal species. Therefore, expression of the porcine A-O blood group determinants which cross-react with anti-human blood group H and A antibodies might be influenced by the FUT2 gene.

Further information about blood groups and E. coli swine diseases include that carbohydrate structures of blood group antigens mediate the adhesion of some pathogenic microorganisms to host tissues, e.g. Helicobacter pylori adhere to Lewis$^b$ blood group antigens, and E. coli causing urinary tract infections adhere to blood group P substance. Genes encoding glycosyltransferases that are responsible for the formation of the blood group specific carbohydrate structures, therefore, represent candidate genes for the control of bacterial colonization by the host. The localization of these genes is in the same chromosomal region as the locus responsible for adhesion/non-adhesion of F18 positive E. coli in the swine small intestine. Swine do not express blood group antigens A and O until after weaning, this is the same time that they become susceptible to disease caused by F18 E. coli.

New methods of diagnosis and treatment are needed for E. coli related intestinal diseases in swine. Detection of a genetic mutation was proposed as a diagnostic test for some swine disorders (malignant hyperthermia) (Fujii et al., 1991; U.S. Pat. No. 5,358,649), but polymorphic markers were not reported for diagnosis. Vaccines to develop resistance to E. coli colonization were described (U.S. Pat. No. 5,552,144; WO 8604604), but are unlikely to be a preferred method to prevent the E. coli disease because of difficulties in administering live vaccine orally to newborn swine, and because of regulatory restrictions. Antibiotics are available for treatment, but there is no successful prophylaxis.

Compositions and non-invasive methods are available for the identification of swine genetically resistant to E. coli related diseases, in particular, intestinal diseases associated with a strain of E. coli bacteria supplied with F18 fimbriae. DNA polymorphisms in the swine alpha (1,2) fucosyltransferase (FUT1) gene were identified that differentiate resistant from susceptible swine and provide a diagnostic test useful for swine breeders. However, further improvements in disease control and weight gain are desirable.

Understanding and controlling the decreased rate of gain in swine fed diets with high levels of SBM would be economically beneficial to the swine industry. If subclinical disease due to E. coli infection is the reason for the decreased rate of gain in swine fed high levels of SBM, preventing or controlling this subclinical disease would be useful.

It has not been determined if diets in which SBM has been replaced with animal-based proteins can prevent subclinical and/or clinical disease due to F18+E. coli or if the decreased rate of gain seen in swine fed diets with high levels of SBM is due to subclinical disease. Additionally, it is not known if diet and genetics can interact in preventing disease due to F18 E. coli.

SUMMARY OF THE INVENTION

A method for improving weight gain in swine has the following steps: selecting swine that are genetically resistant to E. coli colonization and feeding the selected swine high levels of a plant-based protein concentrate, wherein high levels are generally about 20% or greater. A suitable plant-based protein concentrate is SBM. The selecting includes determining in a biological sample from the swine whether or not adenine is the only nitrogen base at position 307 in alpha 1,2 fucosyltransferase gene, and feeding the swine of this genotype high SBM diets. A further method of preventing F18 E. coli colonization in swine is by replacing some or all of the plant-based proteins in the diet fed to the swine, with animal-based proteins. Suitable animal-based proteins include milk, plasma and fish meal. This is particularly efficient for swine genetically susceptible to F18 E. coli colonization, that is, swine that do not have only adenine as the nitrogen base at position 307 in the swine alpha 1,2 fucosyltransferase.

BRIEF DESCRIPTION OF THE DRAWINGS

FIG. 1 shows the nucleotide sequence (FUT1) (below) SEQ ID NO:1 and the predicted amino acid sequence (above) SEQ ID NO:2 of the swine α1→2fucosyltransferase polymorphism of the present invention using the one-letter amino acid code. The solid double line below the amino acid sequences (=) is the putative transmembrane region: the dotted line below the amino acid sequence shows two potential N-linked glycosylation sites ( . . . ).

□ is where an adenine (A) is substituted for guanine (G) in resistant swine. This is position 307 of the open reading frame (ORF).

* Indicates the termination codon.

Abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val, W, Trp; and Y, Tyr.

FIG. 2 presents the effect of genetic resistance to F18 and diet on weight gain in weaned swine challenged with F18 E. coli on days 4, 6, 8 and 10 days post weaning.

FIG. 3 shows the effect of genetic resistance to F18 and diet on fecal shedding of F18 *E. coli.*

FIG. 4 shows the effect of genetic resistance to F18 and diet on weight gain in unchallenged, control swine.

FIG. 5 shows the relative amounts of fecal shedding of F18 *E. coli* in genetically susceptible swine fed either cows milk (n=6) or a high SBM diet (n=6).

FIG. 6 shows the relative amounts of fecal shedding of F18 *E. coli* in genetically susceptible littermates suckling sows milk (n=5) or weaned at 17 days of age and fed the high SBM diet (n=5).

DESCRIPTION OF THE INVENTION

The present invention relates interactions between genotype and diet that are useful in the dietary control of intestinal disease. Compositions are related that are useful to differentiate, with a high level of sensitivity and specificity, swine that are genetically resistant to a reduced rate of gain when fed diets containing high levels of SBM. The reduced rate of gain can also be prevented by reducing the levels of SBM in nursery diets and replacing a majority of the soy bean meal with animal-based protein sources, fish meal, plasma or milk. Using these strategies, genetically resistant swine fed the diet low in SBM, or a diet high in SBM, and susceptible swine fed a diet low in SBM were not colonized by F18+*E. coli* and gained weight at an acceptable rate (FIGS. 2 and 3; groups 1, 2, and 4).

Only swine determined to be susceptible to F18 *E. coli* using the PCR-RFLP test described herein and fed a diet high in soy bean meal developed clinical or subclinical edema disease, shed high levels of F18 *E. coli* after challenge, and had a low rate of gain relative to the other swine in the trial (FIGS. 2 and 3; group 3).

Swine found to be genetically resistant on the basis of the PCR-RFLP test did not express intestinal receptors for F18 *E. coli* regardless of diet and did not develop disease.

Surprisingly, susceptible swine fed the diet with low levels of SBM and fish meal and plasma expressed the intestinal receptor for F18 *E. coli,* as determined by the microscopic adhesion test, (see Example 2 herein) but were not colonized. This novel mechanism of resistance is not due to expression of intestinal receptors. Only genetically susceptible swine fed a high SBM diet developed disease, demonstrating an interaction of diet and genetics in disease susceptibility.

Milk was also useful preventing disease associated with colonization by F18 *E. coli.* Genetically susceptible swine were weaned and fed either (a) a diet high in SBM, (b) cows' milk or (c) milk directly from the sow. The results indicate that swine fed the diet high in SBM developed disease more frequently, shed higher levels of F18 *E. coli* (FIGS. 5 and 6), and developed vascular lesions after experimental challenge at higher levels than did swine fed milk only. Milk, unlike the diets containing plasma and fish meal, prevented the expression of intestinal receptors for *E. coli.* Taken together, the data demonstrates the novel interaction of diet, genetics, intestinal receptor level and disease susceptibility. Thus, disease and the associated reduced rate of gain can be controlled by a variety of factors which operate via different mechanisms. Manipulation of these factors by the methods and compositions of the present invention, improves swine survival and quality.

A non-invasive method for identifying a swine that is resistant to intestinal colonization by *E. coli* includes the following steps: determining whether a genetic polymorphism associated with resistance to colonization is in a biological sample from the swine; and inferring that the swine is resistant if the swine is homozygous for the polymorphism.

More particularly, the method is determining in a biological sample from the swine whether the only nitrogen base at position 307, starting with the ATG codon as position 1, in the alpha (1,2) fucosyltransferase gene (FIG. 1) of the swine is adenine; and identifying the swine as resistant if the only nitrogen base at position 307 is adenine.

To determine whether a polymorphism is present in a biological sample, restriction fragment length polymorphisms are analyzed on a gel that separates them by molecular weight. Restriction endonucleases are enzymes that reproducibly cut nucleic acid molecules at specific sites, resulting in nucleic acid fragments of different molecular weights, depending on the location of the cuts.

Breeding swine to be resistant to *E. coli* associated diseases is accomplished by selecting for breeding swine that have a genetic polymorphism in the alpha (1,2) fucosyltransferase 1 gene that identifies them as swine that are resistant to *E. coli* related intestinal diseases; and breeding the selected swine by methods known to those of skill in the art.

A DNA molecule which is polymorphic for the alpha (1,2) fucosyltransferase 1 gene in swine has, for example, a sequence in accordance with FIG. 1.

Polypeptides encoded by the polymorphic DNA molecules of the present invention have alpha (1,2) fucosyltransferase activity.

A molecular assay for detecting *E. coli* F18 receptors in swine is to (a) isolate DNA from porcine nucleated cells; (b) amplify the DNA in a polymerase chain reaction (PCR) using oligonucleotides as primers which are complementary to a DNA sequence of the porcine alpha (1,2) fucosyltransferase gene 1; (c) perform a restriction enzyme digest with at least one restriction enzyme e.g., HinPI; (d) separate the resulting fragments by gel electrophoresis; (e) determine the respective numbers and lengths of fragments on the gel; and (f) determine from the numbers and length of fragments, which receptors are present in the porcine cells.

A kit for detecting polymorphisms associated with *E. coli* F18 receptors uses oligonucleotides in separate containers which are complementary to a DNA sequence of the porcine alpha (1,2) fucosyltransferase gene 1 that distinguishes resistant from sensitive swine. The test can be performed on swine of any age. The kit includes in separate containers, enzymes and primers to amplify DNA, e.g., by PCR, restriction enzymes, positive and negative control DNAs.

The polymorphisms are also useful to develop drugs to treat swine that have *E. coli*-associated disease. A mutated form of porcine alpha 1,2 fucosyltransferase could interfere with the normal enzyme, preventing it from producing the intestinal receptor for F18.

Molecular analysis of DNA polymorphisms associated with resistance of swine to *E. coli* associated diseases facilitated diagnostic assays to select resistant swine for breeding. Resistant swine differ from sensitive swine at the *E. coli* F18 receptor locus as identified by the polymorphic markers of the present invention.

The DNA polymorphism in the swine alpha (1,2) fucosyltransferase (FUT1) gene that differentiates resistant from susceptible arose by a mutation (change) in a nucleotide sequence leading to a new allele. An allele is a condition of a gene. In a population there may be many alleles of a gene differing by nitrogen base substitutions, presumably caused by mutations in an ancestral DNA molecule. The coexistence in a population of more than one allele (sometimes referred to as a "variant") is called a genetic polymorphism. Loci at which more than one allele may exist as apparently stable components of a population, is a polymorphic locus. Usually, one of the polymorphic loci is at a low frequency in the population.

As determined from a biological sample, preferably blood, the resistant swine have a polymorphism in their genomes in which the only base detected at position 307 of the ORF (see FIG. 1) in the nucleotide sequence is adenine, whereas the base in the same position in homozygous susceptible swine is guanine. Heterozygous swine will show both types of DNA and will be susceptible. The polymorphism is a variation of a porcine gene sequence (Cohney et al., 1996). There are various polymorphisms at bp position 307.

In order to obtain candidate genes for the *E. coli* F18 receptor locus (ECF18R) one genomic clone containing the gene was isolated containing the alpha (1,2) fucosyltransferase gene, FUT1 from a porcine genomic library. Mapping by direct PCR placed the gene in band q11 of porcine chromosome 6 (SSC6q11). Sequence analysis of the cosmids resulted in the characterization of an open reading frame (ORF), 1098 base pairs in length, that is 82.3% identical to the human FUT1 sequence. The FUT1 loci—therefore seem to be porcine equivalents of the human blood group H. The M307 mutation is a good marker for marker-assisted selection of *E. coli* F18 adhesion resistant animals.

FIG. 1 shows the nucleotide sequence (FUT1) (below) and the predicted amino acid sequence (above) of the swine α1→2fucosyltransferase polymorphism of the present invention using the one-letter amino acid code. The solid double line below the amino acid sequences (=) is the putative transmembrane region: the dotted line below the amino acid sequence shows two potential N-linked glycosylation sites ( . . . ).

☐ is where an adenine (A) is substituted for guanine (G) in resistant swine. This is position 307 of the open reading frame (ORF).

\* Indicates the termination codon.

Abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

FIG. 2 presents the effect of genetic resistance to F18 and diet on weight gain in weaned swine challenged with F18 *E. coli* on days 4, 6, 8 and 10 days post weaning. All swine were weighed during the study and the average weight gain was determined for each group. Group 1 was genetically resistant, low SBM diet, group 2 was genetically susceptible, low SBM diet, group 3 was genetically susceptible, high SBM diet, group 4 was genetically resistant, high SBM diet. All groups had 10 swine except for group 1 which had 11 swine. Group 3 swine gained weight at a significantly lower rate than did the other 3 groups.

FIG. 4 shows the effect of genetic resistance to F18 and diet on weight gain in unchallenged, control swine. All swine were weighed during the study and the average weight gain as determined for each group. Group 1 was genetically resistant, low SBM diet, group 2 was genetically susceptible, low SBM diet, group 3 was genetically susceptible, high SBM diet, and group 4 was genetically resistant, high SBM diet. All groups had 10 swine. All groups gained weight at a similar rate.

FIG. 3. shows the effect of genetic resistance to F18 and diet on fecal shedding of F18 *E. coli*. Swine were challenged with F18 *E. coli* on days 4, 6, 8 and 10 days post weaning. Fecal samples were collected during the study and F18 *E. coli*. was enumerated by quantitative bacteriology and mean shedding determined for each group. Group 1 was genetically resistant, low SBM diet, group 2 was genetically susceptible, low SBM diet, group 3 was genetically susceptible, high SBM diet, and group 4 was genetically resistant, high SBM diet. Group 3 shed significantly more F18 *E. coli* than did the other 3 groups during this trial.

FIG. 5 shows the relative amounts of fecal shedding of F18 *E. coli* in genetically susceptible swine fed either cows milk (n=6) or a high SBM diet (n=6). Swine were challenged with F18 *E. coli* on days 4, 6, 8 and 10 days post weaning. Fecal samples were collected during the study and F18 *E. coli* enumerated by bacteriology and mean shedding determined for each group. Swine fed cow's milk shed significantly less F18 *E. coli* than did swine fed the high SBM diet during the study.

FIG. 6 shows the relative amounts of fecal shedding of F18 *E. coli* in genetically susceptible littermates suckling sows milk (n=5) or weaned at 17 days of age and fed the high SBM diet (n=5). Swine were challenged with F18 *E. coli* at 21 days of age. Fecal samples were collected during the study and F18 *E. coli* was enumerated by quantitative bacteriology and mean shedding was determined for each group. The swine on the sow shed less F18 *E. coli* that did the weaned swine fed the high SBM diet.

EXAMPLES

The following examples provide illustrative methods, compositions and embodiments of the present invention.

Examples 1

An Assay for Swine Resistant to F18 *E. Coli* Colonization

The polymorphisms used to differentiate genetically susceptible to F18 *E. coli* colonization, from resistant swine are easily identified using— PCR-RFLP tests. One embodiment of the tests used a 160 bp fragment of porcine alpha (1,2) fucosyltransferase 1 amplified using PCR with the following primers; 5'CCAACGCCTCCGATTCCTGT3' and SEQ ID NO:3 5'GTGCATGGCAGGCTGGATGA3'. SEQ ID NO:4 Preferred PCR conditions for this embodiment are 25 cycles at the following times and temperatures: 94° C., 30 sec; 60° C., 45 sec; 72° C., 90 sec. The amplified DNA from resistant swine was digested by the restriction enzyme Hgal, but was not digested by the restriction enzyme HinPI. The amplified DNA from homozygous susceptible swine was digested by the restriction enzyme HinPI. The amplified DNA from heterozygous susceptible swine was partially digested by both enzymes.

Example 2

Sensitivity and Specificity of an Assay Using Alpha (1,2) Fucosyltransferase in Detecting Swine Resistant to F18 *E. Coli*

A study was conducted to determine the association between disease resistance and the polymorphism at position 307 of the FUT1 gene. 183 weaned swine (ranging in ages 2–6 months) were obtained from six different breeding herds. Only one of these herds was known to contain resistant animals before the start of the study, and this herd is known to have a high incidence of porcine stress syndrome. The other 5 herds had no evidence of porcine stress syndrome, and the incidence of disease resistance was unknown. Swine from each herd were randomly selected, humanely euthanized and spleens and samples of small intestine were removed. DNA was extracted from splenic tissue and used in a PCR-RFLP assay described in Example 1. The microscopic adhesion test was performed as follows: intestinal cells were purified by scraping the mucosal surface off the intestine, lysing the cells in a hypotonic EDTA solution and washing by centrifugation. The purified intestinal cell brush borders were incubated with F18 $E.$ $coli$. This mixture was examined by phase contrast microscopy. This assay determined if swine were susceptible (intestinal samples had adhering bacteria) or resistant (intestinal samples had no adhering bacteria). The PCR-RFLP assay for the polymorphism correlated with the bacteria-intestinal cell binding assay in 53 of 53 resistant swine and 128 of 130 susceptible swine. Two swine that were determined susceptible using the bacteria-intestinal cell binding assay were incorrectly predicted to be resistant using the PCR-RFLP assay. Two of the six herds examined contained resistant swine, while only one herd had porcine stress syndrome, demonstrating that the PCR-RFLP assay can identify disease resistant animals in animals that do not have porcine stress syndrome.

Example 3

Composition and use of Diet in Genetically Susceptible and Resistant Swine to Prevent Intestinal Disease in Weaned Swine Eighty-one weaned swine were obtained from one breeding herd. Before weaning, small sections of ears were obtained from the swine and DNA was extracted from the sections. A PCR-RFLP procedure was conducted on the DNA to predict if animals were genetically susceptible or resistant (Example 1). Of the 81 swine, 41 were predicted to be genetically resistant and 40 were predicted to be genetically susceptible. Forty-one of these 81 swine were randomly selected challenged with an F18 $E.$ $coli$ on days 4, 6, 8 and 10 days after weaning as previously described (Bosworth et al., 1996). These forty-one swine were in one of the four following groups; (1) genetically resistant, high SBM diet; (2) genetically resistant, low SBM diet; (3) genetically susceptible, high SBM diet; and (4) genetically susceptible, low SBM diet; (FIGS. 2 and 3, groups 1–4 respectively). All groups had 10 swine, except for group 1 which had 11 swine.

Samples of brain and intestine were also collected at the end of the study (three weeks after weaning) fixed in formalin, stained and examined by light microscopy for the presence of vascular lesions. Groups 1, 2, and 4 had similar rates of gain, and shed low levels of F18 $E.$ $coli$. None of these 31 swine had clinical disease due to F18 $E.$ $coli$ or any evidence of vascular lesions. Group 3 had a significantly lower rate of gain (FIG. 1, $p<0.01$) and shed more F18 $E.$ $coli$ than did groups 1, 2 and 4 (FIG. 2, $p<0.01$, Student's t-test). Two of the 10 swine in group 3 developed clinical edema disease, and nine of 10 developed vascular lesions in the brain or intestine. The presence of vascular lesions and reduced rate of gain in group 3 swine is characteristic of subclinical edema disease.

The remaining 40 swine were assigned to the same type of groups on the basis of diet and genotype as above. However, none of these animals in these 4 groups (n=10) were challenged with $E.$ $coli$, therefore, these served as negative controls. All 4 of these control groups had a similar rate of gain (FIG. 3), none developed clinical disease or vascular lesions, and no F18 $E.$ $coli$ were found in these animals before, during and at the conclusion of the study. At the conclusion of the study (3 weeks after weaning) all animals were humanely euthanized, and the microscopic adhesion assay was performed. Intestinal cells were purified by scraping the intestinal mucosa, lysing the cells in hypotonic EDTA, and washing by centrifugation. The purified brush borders were incubated with F18 $E.$ $coli$, and this mixture was examined by phase contrast microscopy to determine if the swine lacked intestinal receptors (classified as resistant) or expressed intestinal receptors (classified as susceptible). A total of 81 animals was determined to be either susceptible or resistant on the basis of the PCR-RFLP test and on the basis of the ability of F18 $E.$ $coli$ to adhere to intestinal samples. These two tests were in 100% agreement. Only the 40 swine determined to be genetically susceptible on the basis of the PCR-RFLP test had intestinal receptors, and the 41 genetically resistant swine did not express receptors. These diets did not appear to influence the expression of intestinal receptors as determined by the microscopic adhesion test.

This experiment demonstrates that either diet alone or genotype alone can prevent disease due to F18 $E.$ $coli$. The ability to use a relatively inexpensive high SBM diet in resistant swine demonstrates the positive interactions of these two separate preventive measures. The ability to prevent disease by feeding susceptible swine low SBM diets, extends the protection of herds that are genetically mixed with regard to $E.$ $coli$ susceptibility.

Example 4

Composition and use of Diet to Reduce Expression of Intestinal Receptors for F18 $E.$ $Coli$ and Prevent Disease Twelve genetically susceptible swine were weaned at 3 weeks of age and fed either (a) a diet containing high levels of SBM or (b) cows milk. All animals were challenged with $E.$ $coli$ at 4, 6, 8 and 10 days postweaning as described herein. At the conclusion of the study (2 weeks after challenge) all animals were humanely euthanized and intestinal cells were purified by scraping the intestinal mucosa, lysing the cells in hypotonic EDTA and washing by centrifugation. The purified brush borders were incubated with F18 $E.$ $coli$ and this mixture was examined by phase contrast microscopy. Samples of brain and intestine were also collected at necropsy, fixed in formalin and stained and examined for the presence of vascular lesions with light microscopy. Five of the six swine fed the SBM diet developed vascular lesions in the brain or intestines, and one animal developed clinical edema disease. Only one of the six animals fed cow's milk developed vascular lesions, and none developed clinical edema disease. Bacterial shedding of F18 $E.$ $coli$ was less in swine fed milk than in swine fed the diet high in SBM (FIG. 5). Weight data was not compared in this experiment, because the diets were too different in composition to allow valid comparisons. The in vitro microscopic adhesion assay was used to determine if the intestinal receptor for F18 $E.$ $coli$ was expressed. Only 1 of 6 animals fed cows milk was determined to have receptors for F18 $E.$ $coli$, while all six swine fed the high SBM diet did.

In a separate experiment, five swine from one litter were weaned at 17 days of age and the remaining five swine remained on the sow. The weaned swine were fed a diet high in SBM while the swine that remained on the sow suckled the sow's milk. At 21 days of age, all swine were challenged with F18 *E. coli* as previously described (Bosworth et al., 1996). At the conclusion of the study (10 days after challenge) all animals were humanely euthanized and intestinal cells were purified by scraping the intestinal mucosa, lysing the cells in hypotonic EDTA and washing by centrifugation. The purified brush borders were incubated with F18 *E. coli* and this mixture was examined by phase contrast microscopy. Samples of brain and intestine were also collected at necropsy, fixed in formalin and stained and examined for the presence of vascular lesions with light microscopy. Four of the five swine fed the SBM diet developed vascular lesions in the brain or intestines. Only one of the five animals fed sow's milk developed vascular lesions. No animal developed clinical edema disease. Bacterial shedding of F18 *E. coli* was less in swine fed milk than in swine fed the diet high in SBM ($p<0.01$; FIG. 6). The microscopic adhesion assay was used to determine if the intestinal receptor for F18 *E. coli* was expressed. Only 1 of 5 animals fed cows milk was determined to have receptors for F18 *E. coli* while all five swine fed the high SBM diet did. FIG. 2 presents the effect of genetic resistance to F18 and diet on weight gain in weaned swine challenged with F18 *E. coli* on days 4, 6, 8 and 10 days post weaning. FIG. 3 shows the effect of genetic resistance to F18 and diet on fecal shedding of F18 *E. coli*. FIG. 4 shows the effect of genetic resistance to F18 and diet on weight gain in unchallenged, control swine. FIG. 5 shows the relative amounts of fecal shedding of F18 *E. coli* in genetically susceptible swine fed either cows milk (n=6) or a high SBM diet (n=6). FIG. 6 shows the relative amounts of fecal shedding of F18 *E. coli* in genetically susceptible littermates suckling sows milk (n=5) or weaned at 17 days of age and fed the high SBM diet (n=5).

Materials and Methods

1. Primers

Primers derived from the human FUT1 gene were used for the amplification of its porcine counterpart from genomic DNA. From the resulting porcine sequences specific primers were designed which were used in further amplification and sequencing reactions.

2. Screening of a Porcine Genomic Library

Porcine genomic libraries were obtained from Clonetech and screened with porcine but FUT1 cDNA. After hybridization of replica filters at 42° C. for 15h (50% formamide, 6×SSC, 5×Denhardt's, 0.5% SDS, 0.1 mg/ml Salmon Sperm) and washing twice at 65° C. for 30 min. (1×SSC, 0.1% SDS), positive colonies were identified after exposure (15 h, −80° C.) to X-ray film.

3. Chromosomal Mapping of FUT1

The FUT1 gene was mapped using direct in situ chromosomal PC (DISC PCR) on porcine metaphases.

4. Subcloning

Enzymatic digests of probe positive genomic colonies were separated on agarose gel, transferred to a nylon membrane, and probe positive bands were subcloned into plasmids for FUT sequencing. The sequence of FUT1 derived from a subclone is shown in FIG. 1.

5. Polymerase Chain Reaction and Direct Sequencing

Using the Perkin Elmer Ready Reaction Dye Terminator kit (Perkin Elmer Cetus, Norwalk, Conn., USA) and 10 pmol of primer, cycle sequencing was performed with a thermal program consisting of an initial denaturation of 5 min at 95° C., followed by 25 cycles of 30 sec 95° C., 15 sec 50° C. and 4 min 60° C. Samples were analyzed on a 373A ABI sequencer (Applied Biosystems Inc.) and sequence analysis was performed with the GCG package (Devereux, 1984).

6. Examples of Low and High SBM Diets

Table 1 lists ingredients in a low SBM diet which is relatively expensive. Table 2 lists ingredients in a high SBM diet which is relatively inexpensive.

7. Statistical Methods

Analysis of variance was used to compare groups as shown in the FIGS.

TABLE 1

COMPLEX DIET[1]: LOW SOYBEAN MEAL, RELATIVELY EXPENSIVE

| Composition | | Nurient Concentration | | |
|---|---|---|---|---|
| Ingredient | % of Diet | Nutrient | Unit | Amount in Diet |
| Milk By-products | 26.00 | Crude Protein | % | 21.40 |
| Feeding Oatmeal | 24.50 | Total Lysine | % | 1.50 |
| Fine Grind Corn | 12.40 | Available Lysine | % | 1.35 |
| Ground Soybean Meal | 13.50 | Available Met + Cys | % | 0.76 |
| Fish Meal | 9.30 | Available Tryptophan | % | 0.28 |
| Plasma | 5.00 | Available Threonine | % | 0.81 |
| Essential Amino Acids | 0.35 | Available Isoleucine | % | 0.76 |
| Vitamins and Minerals | 3.55 | Available Valine | % | 0.96 |
| Fat | 3.30 | Lactose | % | 22.00 |
| Soy Hulls | 2.10 | Metab. Energy | Kcal/lb | 1530.00 |
| Total | 100% | Crude Fiber | % | 2.70 |
| | | Calcium | % | 0.95 |
| | | Total Phosphorus | % | 0.80 |
| | | Salt Equivalent | % | 1.12 |
| | | Total Magnesium | % | 0.16 |
| | | Total Potassium | % | 1.22 |
| | | Copper added | PPM | 175.00 |
| | | Selenium added | PPM | 0.30 |
| | | Zinc added | PPM | 128.00 |
| | | Vitamin E | IU/lb | 40.00 |

[1]Non-medicated.

Diet Composition and Nutrient Content

TABLE 2

SIMPLE DIET[2]: HIGH SOYBEAN MEAL, RELATIVELY INEXPENSIVE

| Composition | | Nurient Concentration | | |
|---|---|---|---|---|
| Ingredient | % of Diet | Nutrient | Unit | Amount in Diet |
| Milk By-products | 0.00 | Crude Protein | % | 23.90 |
| Feeding Oatmeal | 20.00 | Total Lysine | % | 1.50 |
| Fine Grind Corn | 35.70 | Available Lysine | % | 1.35 |
| Ground Soybean Meal | 30.00 | Available Met + Cys | % | 0.76 |
| Fish Meal | 6.10 | Available Tryptophan | % | 0.28 |
| Plasma | 0.00 | Available Threonine | % | 0.81 |
| Essential Amino Acids | 0.35 | Available Isoleucine | % | 0.88 |
| Vitamins, Minerals, Salt | 4.22 | Available Valine | % | 1.05 |
| Fat | 2.50 | Lactose | % | 0.00 |
| Soy Hulls | 2.10 | Metab. Energy | Kcal/lb | 1530.00 |
| Total | 100% | Crude Fiber | % | 2.70 |
| | | Calcium | % | 0.97 |
| | | Total Phosphorus | % | 0.80 |
| | | Salt Equivalent | % | 1.12 |
| | | Total Magnesium | % | 0.19 |
| | | Total Potassium | % | 1.22 |
| | | Copper added | PPM | 175.00 |
| | | Selenium added | PPM | 0.30 |
| | | Zinc added | PPM | 128.00 |
| | | Vitamin E | IU/lb | 40.00 |

[2]Non-medicated.

Documents Cited

Bertschinger et al. (1993) *Veterinary Microbiology* 35:79–89.
Bosworth et al. (1996) *Infection and Immunity* 64:55–60.
Cohney et al. (1996) *Immunogenetics* 44:76–79.
Devereux et al. (1984) *Nucleic Acids Res.* 1:387–395.
Fujii et al. (1991) *Science* 253:448–451.
Kelly et al. (1994) *Proc. Natl. Acad. Sci., U.S.A.* 91:5843–5847.
Li et al. (1991) *J. of Animal Sci.* 69:3299–3307.
Meijerink, E. et al., (1997) 25th *Int. Conf. On Animal Genetics*, p. 44.
Nagy et al., (1992) *Infection and Immunity* 60:1285–1294.
Vögeli et al. (1996) *Animal Genetics* 27:321–328.
U.S. Pat. No. 5,358,649, Maclennon et al.
U.S. Pat. No. 5,552,144, Valery et al.
WO 8604604, Peterson.
WO 9628967, Koike, C.
WO 9413811, Imberechts and Lintermans.

We claim:

1. A method for improving weight gain in swine that are susceptible to F18 *E. coli* colonization and challenged by F18 *E. coli,* said method comprising:

a) selecting susceptible, challenged swine having a base other than adenine at position 307 of the nucleotide sequence encoding FUTI as set forth in SEQ ID NO: 1; and b) feeding said susceptible, challenged swine, postweaning, a nursery diet comprising at least 40% animal-based proteins that results in improved weight gain in said swine.

2. A method of reducing F18 *E. coli* colonization in weanling swine that are genetically susceptible to F18 *E. coli* colonization, wherein said susceptible swine have a base other than adenine at position 307 of the nucleotide sequence encoding FUTI as set forth in SEQ ID NO: 1, and wherein said susceptible swine have been challenged by said F18 *E. coli,* said method comprising replacing at least 34% of the plant-based proteins in a diet fed to the swine with animal-based proteins and thereby reducing F18 *E. coli* colonization in swine fed said animal-based proteins as measured by reduced fecal shedding.

3. The method of claim 2, wherein the animal-based proteins comprise milk, plasma, fish meal, and other animal derived proteins.

4. The method of claim 2, wherein the genetically susceptible swine comprise at least one allele of a nucleic acid sequence encoding FUTI as set forth in SEQ ID NO: 1 has a base other than adenine at position 307.

5. A method of reducing the frequency of clinical disease associated with colonization of F18 *E. coli* in susceptible swine, said method comprising:

a) selecting genetically susceptible swine having a base other than adenine at position 307 of the nucleotide sequence encoding FUTI as set forth in SEQ ID NO: 1; and b) challenging said susceptible swine with F18 *E. coli;* and c) feeding said challenged swine a nursery diet comprising a low level of plant-based proteins, post-weaning, wherein the low level is produced by replacing about 34% of the plant-based proteins with animal-based proteins, and wherein said challenged swine have less clinical disease associated with colonization of F18 *E. coli.*

* * * * *

SEQUENCE LISTING

<160> NUMBER OF SEQ ID NOS: 4

<210> SEQ ID NO 1
<211> LENGTH: 1269
<212> TYPE: DNA
<213> ORGANISM: Swine
<220> FEATURE:
<221> NAME/KEY: CDS
<222> LOCATION: (9)..(1103)
<220> FEATURE:
<223> OTHER INFORMATION: FUT1

<400> SEQUENCE: 1

```
ctcgagcc atg tgg gtc ccc agc cgc cgc cac ctc tgt ctg acc ttc ctg        50
         Met Trp Val Pro Ser Arg Arg His Leu Cys Leu Thr Phe Leu
          1               5                  10 cta gtc tgt gtt tta gca gca att ttc ttc ctg aac gtc tat caa gac         98
Leu Val Cys Val Leu Ala Ala Ile Phe Phe Leu Asn Val Tyr Gln Asp
 15                  20                  25                  30 ctc ttt tac agt ggc tta gac ctg ctg gcc ctg tgt cca gac cat aac        146
Leu Phe Tyr Ser Gly Leu Asp Leu Leu Ala Leu Cys Pro Asp His Asn
                 35                  40                  45
```

```
gtg gta tca tct ccc gtg gcc ata ttc tgc ctg gcg ggc acg ccg gta      194
Val Val Ser Ser Pro Val Ala Ile Phe Cys Leu Ala Gly Thr Pro Val
            50                  55                  60 cac ccc aac gcc tcc gat tcc tgt ccc aag cat cct gcc tcc ttt tcc      242
His Pro Asn Ala Ser Asp Ser Cys Pro Lys His Pro Ala Ser Phe Ser
            65                  70                  75 ggg acc tgg act att tac ccg gat ggc cgg ttt ggg aac cag atg gga      290
Gly Thr Trp Thr Ile Tyr Pro Asp Gly Arg Phe Gly Asn Gln Met Gly
        80                  85                  90 cag tat gcc acg ctg ctg gcc ctg gcg cag ctc aac ggc cgc cag gcc      338
Gln Tyr Ala Thr Leu Leu Ala Leu Ala Gln Leu Asn Gly Arg Gln Ala
 95                 100                 105                 110 ttc atc cag cct gcc atg cac gcc gtc ctg gcc ccc gtg ttc cgc atc      386
Phe Ile Gln Pro Ala Met His Ala Val Leu Ala Pro Val Phe Arg Ile
                115                 120                 125 acg ctg cct gtc ctg gcg ccc gag gta gac agg cac gct cct tgg cgg      434
Thr Leu Pro Val Leu Ala Pro Glu Val Asp Arg His Ala Pro Trp Arg
            130                 135                 140 gag ctg gag ctt cac gac tgg atg tcc gag gat tat gcc cac tta aag      482
Glu Leu Glu Leu His Asp Trp Met Ser Glu Asp Tyr Ala His Leu Lys
            145                 150                 155 gag ccc tgg ctg aag ctc acc ggc ttc ccc tgc tcc tgg acc ttc ttc      530
Glu Pro Trp Leu Lys Leu Thr Gly Phe Pro Cys Ser Trp Thr Phe Phe
160                 165                 170 cac cac ctc cgg gag cag atc cgc agc gag ttc acc ctg cac gac cac      578
His His Leu Arg Glu Gln Ile Arg Ser Glu Phe Thr Leu His Asp His
175                 180                 185                 190 ctt cgg caa gag gcc cag ggg gta ctg agt cag ttc cgt cta ccc cgc      626
Leu Arg Gln Glu Ala Gln Gly Val Leu Ser Gln Phe Arg Leu Pro Arg
                195                 200                 205 aca ggg gac cgc ccc agc acc ttc gtg ggg gtc cac gtg cgc cgc ggg      674
Thr Gly Asp Arg Pro Ser Thr Phe Val Gly Val His Val Arg Arg Gly
            210                 215                 220 gac tat ctg cgt gtg atg ccc aag cgc tgg aag ggg gtg gtg ggt gac      722
Asp Tyr Leu Arg Val Met Pro Lys Arg Trp Lys Gly Val Val Gly Asp
            225                 230                 235 ggc gct tac ctc cag cag gct atg gac tgg ttc cgg gcc cga tac gaa      770
Gly Ala Tyr Leu Gln Gln Ala Met Asp Trp Phe Arg Ala Arg Tyr Glu
        240                 245                 250 gcc ccc gtc ttt gtg gtc acc agc aac ggc atg gag tgg tgc cgg aag      818
Ala Pro Val Phe Val Val Thr Ser Asn Gly Met Glu Trp Cys Arg Lys
255                 260                 265                 270 aac atc gac acc tcc cgg ggg gac gtg atc ttt gct ggc gat ggg cgg      866
Asn Ile Asp Thr Ser Arg Gly Asp Val Ile Phe Ala Gly Asp Gly Arg
                275                 280                 285 gag gcc gcg ccc gcc agg gac ttt gcg ctg ctg gtg cag tgc aac cac      914
Glu Ala Ala Pro Ala Arg Asp Phe Ala Leu Leu Val Gln Cys Asn His
            290                 295                 300 acc atc atg acc att ggc acc ttc ggc ttc tgg gcc gcc tac ctg gct      962
Thr Ile Met Thr Ile Gly Thr Phe Gly Phe Trp Ala Ala Tyr Leu Ala
            305                 310                 315 ggt gga gat acc atc tac ttg gct aac ttc acc ctg ccc act tcc agc     1010
Gly Gly Asp Thr Ile Tyr Leu Ala Asn Phe Thr Leu Pro Thr Ser Ser
        320                 325                 330 ttc ctg aag atc ttt aaa ccc gag gct gcc ttc ctg ccc gag tgg gtg     1058
Phe Leu Lys Ile Phe Lys Pro Glu Ala Ala Phe Leu Pro Glu Trp Val
335                 340                 345                 350 ggc att aat gca gac ttg tct cca ctc cag atg ttg gct ggg cct         1103
Gly Ile Asn Ala Asp Leu Ser Pro Leu Gln Met Leu Ala Gly Pro
                355                 360                 365
```

-continued

```
tgaaccagcc aggagccttt ctggaatagc ctcggtcaac ccagggccag cgttatgggt    1163
ctccggaagc cccagtaact tccggagatg ctggtggtcc tgtagcaggc tggacactta    1223
tttcaagagt gattctaatt ggctggactc agaggaaacc ctgcag                   1269
```

<210> SEQ ID NO 2
<211> LENGTH: 365
<212> TYPE: PRT
<213> ORGANISM: Swine
<220> FEATURE:
<223> OTHER INFORMATION: FUT1

<400> SEQUENCE: 2

```
Met Trp Val Pro Ser Arg Arg His Leu Cys Leu Thr Phe Leu Leu Val
  1               5                  10                  15

Cys Val Leu Ala Ala Ile Phe Phe Leu Asn Val Tyr Gln Asp Leu Phe
                 20                  25                  30

Tyr Ser Gly Leu Asp Leu Leu Ala Leu Cys Pro Asp His Asn Val Val
             35                  40                  45

Ser Ser Pro Val Ala Ile Phe Cys Leu Ala Gly Thr Pro Val His Pro
         50                  55                  60

Asn Ala Ser Asp Ser Cys Pro Lys His Pro Ala Ser Phe Ser Gly Thr
 65                  70                  75                  80

Trp Thr Ile Tyr Pro Asp Gly Arg Phe Gly Asn Gln Met Gly Gln Tyr
                 85                  90                  95

Ala Thr Leu Leu Ala Leu Ala Gln Leu Asn Gly Arg Gln Ala Phe Ile
                100                 105                 110

Gln Pro Ala Met His Ala Val Leu Ala Pro Val Phe Arg Ile Thr Leu
            115                 120                 125

Pro Val Leu Ala Pro Glu Val Asp Arg His Ala Pro Trp Arg Glu Leu
130                 135                 140

Glu Leu His Asp Trp Met Ser Glu Asp Tyr Ala His Leu Lys Glu Pro
145                 150                 155                 160

Trp Leu Lys Leu Thr Gly Phe Pro Cys Ser Trp Thr Phe Phe His His
                165                 170                 175

Leu Arg Glu Gln Ile Arg Ser Glu Phe Thr Leu His Asp His Leu Arg
            180                 185                 190

Gln Glu Ala Gln Gly Val Leu Ser Gln Phe Arg Leu Pro Arg Thr Gly
        195                 200                 205

Asp Arg Pro Ser Thr Phe Val Gly Val His Val Arg Arg Gly Asp Tyr
    210                 215                 220

Leu Arg Val Met Pro Lys Arg Trp Lys Gly Val Val Gly Asp Gly Ala
225                 230                 235                 240

Tyr Leu Gln Gln Ala Met Asp Trp Phe Arg Ala Arg Tyr Glu Ala Pro
                245                 250                 255

Val Phe Val Val Thr Ser Asn Gly Met Glu Trp Cys Arg Lys Asn Ile
            260                 265                 270

Asp Thr Ser Arg Gly Asp Val Ile Phe Ala Gly Asp Gly Arg Glu Ala
        275                 280                 285

Ala Pro Ala Arg Asp Phe Ala Leu Leu Val Gln Cys Asn His Thr Ile
    290                 295                 300

Met Thr Ile Gly Thr Phe Gly Phe Trp Ala Ala Tyr Leu Ala Gly Gly
305                 310                 315                 320

Asp Thr Ile Tyr Leu Ala Asn Phe Thr Leu Pro Thr Ser Ser Phe Leu
                325                 330                 335
```

```
Lys Ile Phe Lys Pro Glu Ala Ala Phe Leu Pro Glu Trp Val Gly Ile
            340                 345                 350

Asn Ala Asp Leu Ser Pro Leu Gln Met Leu Ala Gly Pro
            355                 360                 365

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
ccaacgcctc cgattcctgt                                          20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
gtgcatggca ggctggatga                                          20
```